United States Patent [19]
Criddle et al.

[11] Patent Number: 5,738,773
[45] Date of Patent: Apr. 14, 1998

[54] FUEL CELLS

[75] Inventors: William James Criddle; Neils Richard Stewart Hansen, both of Penarth, Great Britain

[73] Assignee: Lion Laboratories Plc, South Glamorgan, United Kingdom

[21] Appl. No.: 581,578

[22] PCT Filed: Jul. 8, 1994

[86] PCT No.: PCT/GB94/01489

§ 371 Date: Jan. 16, 1996

§ 102(e) Date: Jan. 16, 1996

[87] PCT Pub. No.: WO95/02817

PCT Pub. Date: Jan. 26, 1995

[30]     Foreign Application Priority Data

Jul. 14, 1993 [GB] United Kingdom .................. 9314609
Jul. 24, 1993 [GB] United Kingdom .................. 9315388

[51] Int. Cl.$^6$ ................................................. G01N 27/26
[52] U.S. Cl. ........................................ 204/411; 204/431
[58] Field of Search ............................... 204/260, 411, 204/431

[56]           References Cited

U.S. PATENT DOCUMENTS

| 3,246,235 | 4/1966 | Allsopp | 204/411 X |
| 4,647,362 | 3/1987 | Watanabe | 204/411 |
| 4,758,325 | 7/1988 | Kanno et al. | 204/411 |
| 5,338,429 | 8/1994 | Jolson et al. | 204/431 X |

FOREIGN PATENT DOCUMENTS

| 0 033 188 | 8/1981 | European Pat. Off. . |
| 0 293 541 | 12/1988 | European Pat. Off. . |
| 0 361 692 | 4/1990 | European Pat. Off. . |
| WO 88/08131 | 10/1988 | WIPO . |

*Primary Examiner*—Stephen Kalafut
*Attorney, Agent, or Firm*—Young & Thompson

[57]           ABSTRACT

A fuel cell sensor (10) comprises a main body (11) in which are mounted working electrodes (12), counter electrodes (13) and respective contacts (14 to 17). The working electrodes (12) are mounted facing each other to define a sample space between them. The electrodes (12) are electrically interconnected in parallel as are the two counter electrodes (13). This arrangement makes it possible to provide a very large working electrode surface area for a small volume sample space (22).

10 Claims, 3 Drawing Sheets

FUEL CELLS

FIELD OF THE INVENTION

This invention relates to fuel cells and in particular, but not exclusively, such cells which act as sensors for oxidisable components in gases.

BACKGROUND OF THE INVENTION

Fuel cells were first invented by Sir William Grove in 1839 and in recent years have been used in many arrangements for the detecting of oxidisable components of gases or vapours, for example in breath testing equipment. Essentially the fuel cell comprises a working electrode or anode and a counter electrode or cathode which are separated by an electrolyte, usually by a porous disc impregnated with an acidic electrolyte. The electrochemical oxidation of the fuel component in the gas results in the development of an electrical potential difference resulting in a flow of electrons from the anode to the cathode and this current and/or potential difference can be detected. One such fuel cell is made by Lion Laboratories Plc.

Although these fuel cells have been successful in a limited field, considerable problems have been experienced both in the time taken for the fuel cell to consume the oxidisable component in the sample and in the time taken for the cell to clear so that it is ready to sense a further sample.

SUMMARY OF THE INVENTION

From one aspect of the invention there is provided a sensor for detecting oxidisable fuel components in a gas or vapour including a pair of working electrodes facing other to define a sample receiving space between them.

This arrangement of facing working electrodes substantially increases the surface area of the working electrode for a given cross-sectional dimension and hence significantly reduces the time taken for a fuel component to contact and hence react with the working electrode. It further enables the working electrodes to be placed very close to one another hence reducing the length of the mean free path available to any fuel component molecule injected into the sample space before it strikes a working electrode. In traditional designs there can be a significant dead space above the single working electrode.

In a preferred embodiment the working electrodes are electrically connected. Further it is preferred that there is a counter electrode for each working electrode and they will be separated from each other by a suitable electrolytically impregnated body. The counter electrodes should also be electrically connected, when this is true of the working electrodes. The respective sets of electrodes can be connected in parallel or in series. In the former arrangement the electrodes could be viewed as being a single cell in a bent configuration, and such an arrangement is included in the invention and indeed other wrapped around arrangemennts may be possible although these may introduce constructional complexities which limit the closest approach of the two working electrode sections.

Preferably the spacing between the working electrodes is between 0.5 mm and 5 mm and a spacing of 1 mm to 2 mm has been found to be a good compromise between cell efficiency and constructional simplicity.

The rate of clearing of the cell may be a function of the net load and it has been found convenient to have a net load of approximately 10 ohms. The sensor may thus have a load resistor across its output which is approximately equal to its impedance.

From another aspect the invention consists in a fuel cell having a closed loop electrical contact for at least one of its electrodes, the loop being substantially circumjacent the operative surface of the electrode.

Traditionally single wire contacts have been used and these can cause local resistance problems and manufacturing difficulties. The use of a closed loop, and preferably annular, contact ensures that there is electrical contact between the electrode and the contact at at least some parts of the contact and removes many localised affects.

The invention also consists in a sensor as described above with the closed loop contact set out above.

Although the invention has been defined above it is to be understood that it includes any inventive combination of the features set out above or in the following description.

BRIEF DESCRIPTION OF THE DRAWINGS

The invention may be performed in various ways and a specific embodiment will now be described by way of example, with reference to the accompanying drawings, in which.

DETAILED DESCRIPTION OF THE INVENTION

Figure 1:
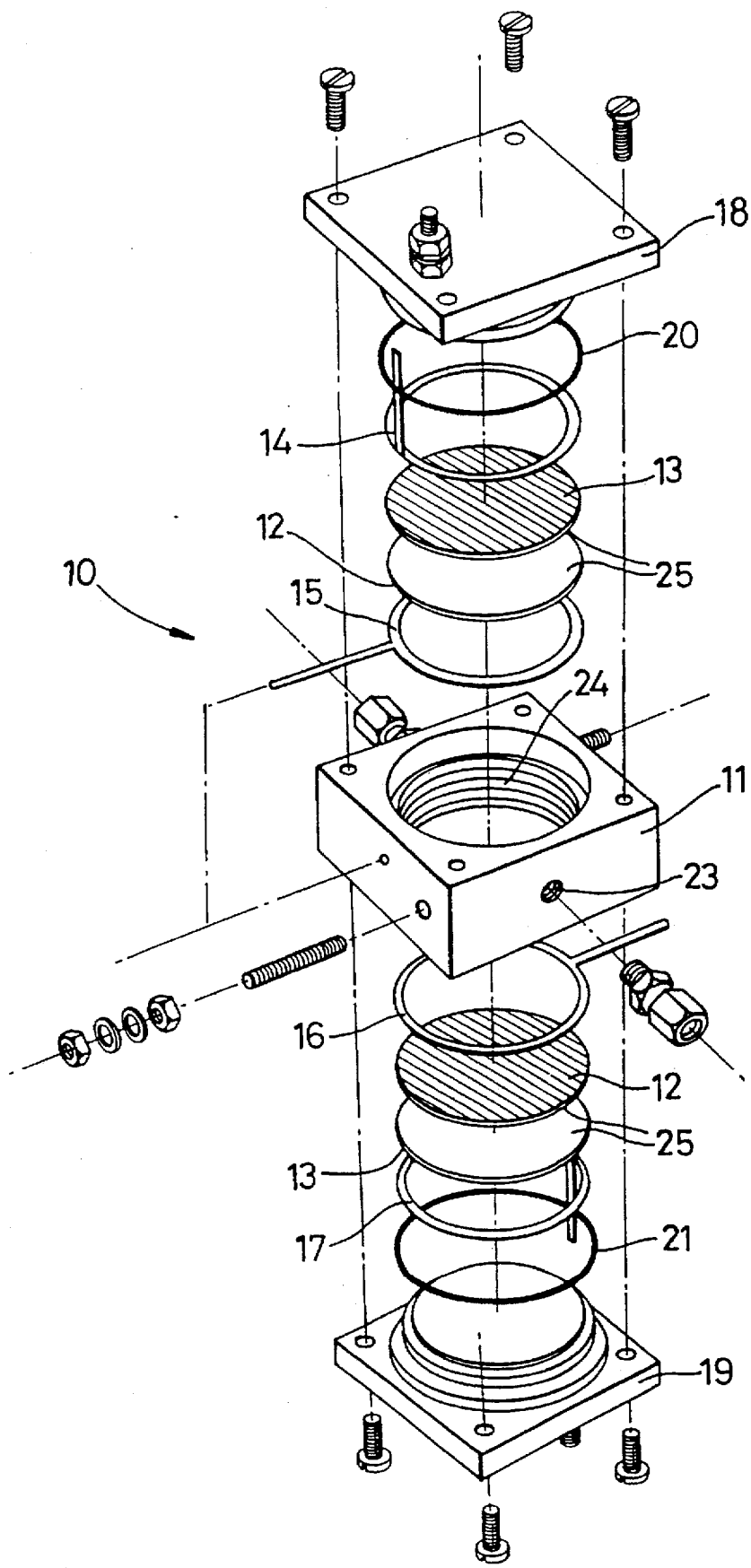
FIG. 1 is an exploded view of one version of a sensor according to the invention.

A fuel cell sensor 10 comprises a main body 11 in which are mounted working electrodes 12, counter electrodes 13 and respective contacts 14 to 17. The main body is closed off by a top cover 18 and a bottom cover 19 and sealed by respective O rings 20 and 21.

The working electrodes 12 are mounted facing each other to define a sample space 22 between them and a sample inlet 23 debouches into this space and an outlet 24 is also connected into it. Each of the electrodes 12,13 comprises a platinum black layer on a micro-porous PVC body and the two bodies 25 in each working/counter electrode pair together contain an acidic electrolyte such as $H_2SO_4$.

Figure 2:
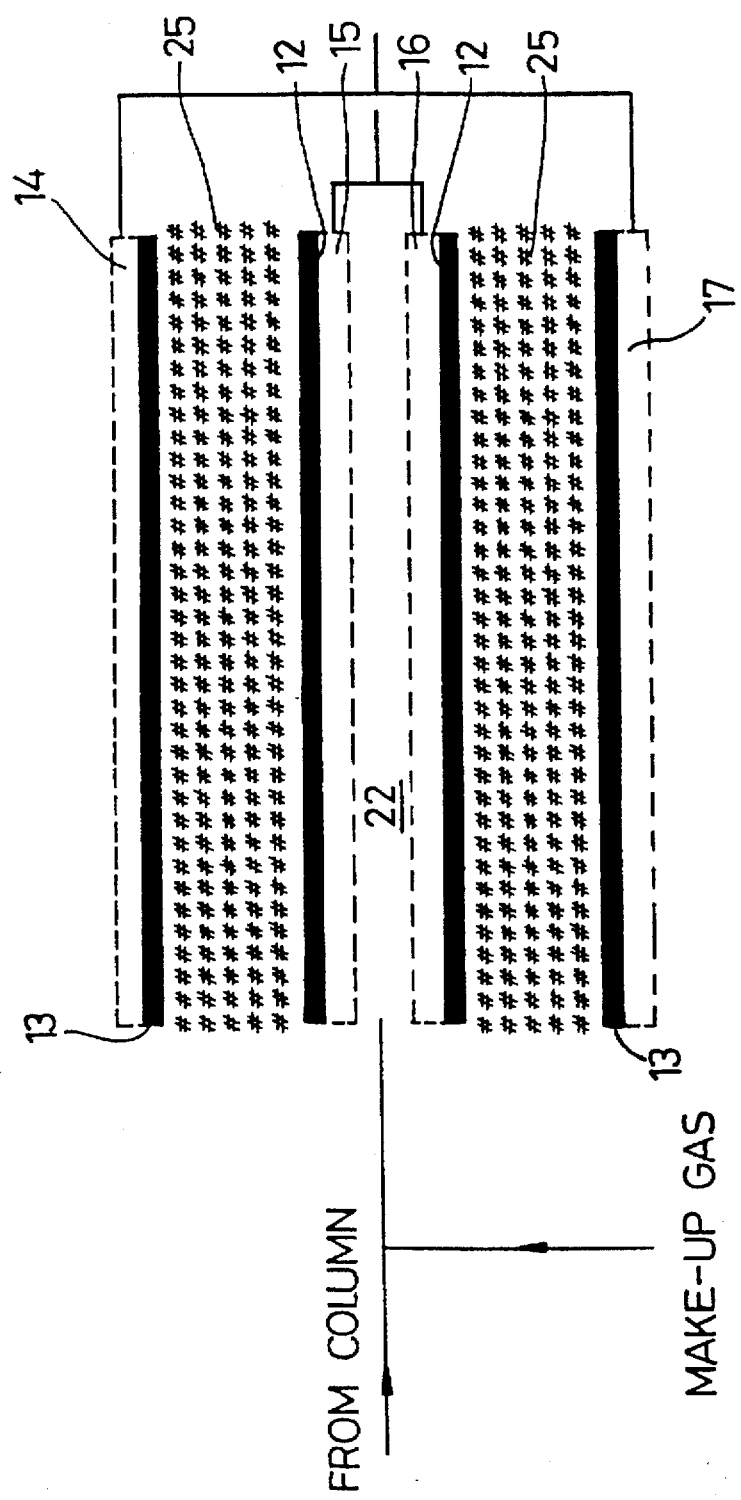
FIG. 2 is a diagrammatic vertical cross-sectional view of the electrodes of the fuel cell illustrating their electrical connections.

As can be seen from FIG. 2 the two working electrodes 12 are electrically interconnected in parallel, as are the two counter electrodes 13. These connections take place through the respective contacts 15 to 17 which are each in the form of gold plated stainless steel annulus which extends around the peripheral margin of its respective electrode.

As has been explained above this configuration allows the working electrodes 12 to be brought very close to each other so that the sample space 22 has a very small volume but a very large working electrode surface area. This results in a sensor which is extremely sensitive, fast to react and which can also clear rapidly.

These characteristics not only mean that a highly sensitive fuel cell is available for traditional existing uses, but also that it can be used for less common purposes such as in gas chromatography (as for example shown in FIG. 2). In that case the cell is designed to perform best with a carrier or make up gas flow through the cell; the sample gas being introduced into this flow. Preferably the make up gas has a 50%–60% relative humidity to prevent drying out of the cell and conveniently it may be nitrogen.

As previously stated, the electrode pairs are connected in parallel and this configuration maximises the current generated.

Figure 3:
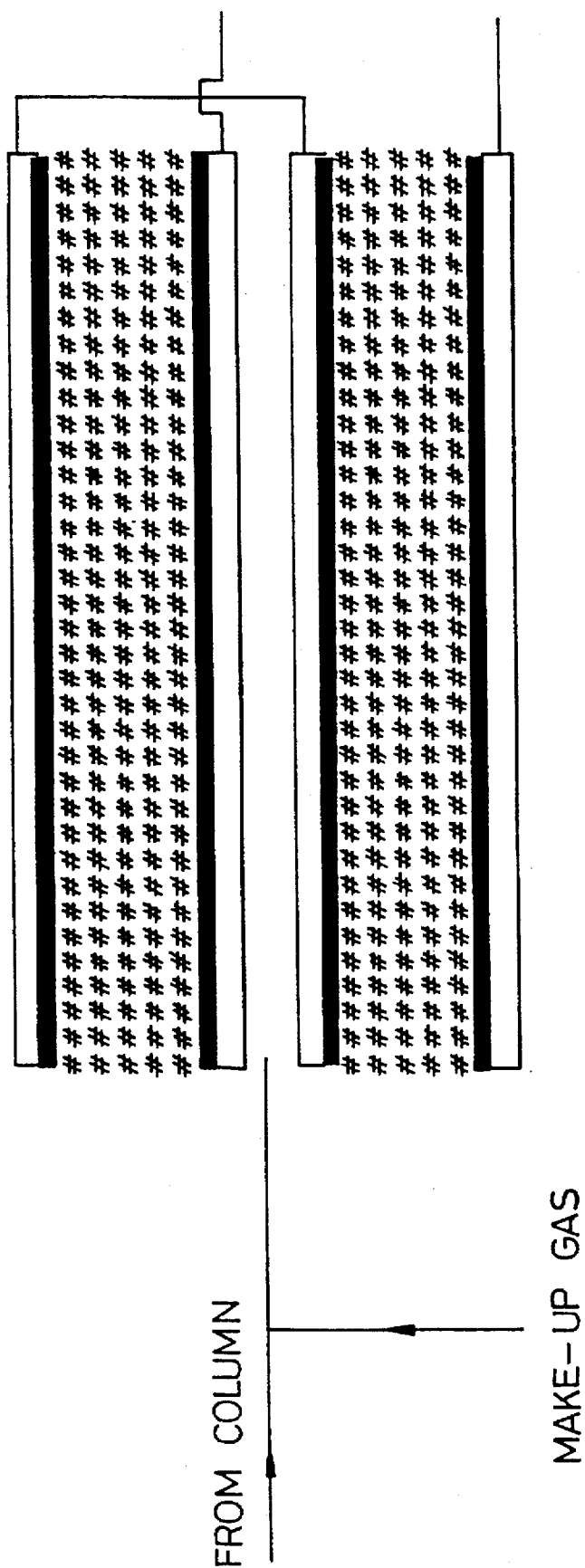
FIG. 3 is the same as FIG. 2, but shows an alternative arrangement of electrical connections.

An alternative series connection is shown in FIG. 3. This arrangement minimises current but maximises the electrical potential of the cell. The configuration chosen would then depend on whether the cell is to be used in either a voltage or current measuring device.

We claim:

1. A fuel cell for detecting oxidizable fuel components in a gas or vapor sample comprising a first and second working electrodes facing each other to define a sample receiving space between them, and a counter electrode for each working electrode, said first working electroded being electrically connected to one of said second working electrode and its associcated counter electrode.

2. A fuel cell as claimed in claim 1, wherein the working electrodes are electrically connected to each other.

3. A fuel cell as claimed in claim 1, wherein an electrolytically impregnated body separates each working electrode from its associated counter electrode.

4. A fuel cell as claimed in claim 1, wherein the counter electrodes are electrically connected to each other.

5. A fuel cell as claimed in claim 1, wherein the sets of electrodes are connected in parallel or in series.

6. A fuel cell as claimed in claim 1, wherein the spacing between the working electrodes is between 0.5 mm and 5 mm.

7. A fuel cell as claimed in claim 6, wherein the spacing is between 1 mm and 2 mm.

8. A fuel cell as claimed in claim 1, wherein the net load for the cell is approximately equal to $10\Omega$.

9. A fuel cell as claimed in claim 1, wherein the fuel cell includes a load resistor across its output which is approximately equal to its impedance.

10. A fuel cell as claimed in claim 1, having a closed loop electrical contact for at least one of its electrodes, the loop being substantially circumjacent the operative surface of the electrode.

* * * * *